US006730621B2

(12) United States Patent
Gott et al.

(10) Patent No.: US 6,730,621 B2
(45) Date of Patent: May 4, 2004

(54) DAMP CLEANSING WIPE

(75) Inventors: Robert Edward Gott, Norwalk, CT (US); Craig Stephen Slavtcheff, Guilford, CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 193 days.

(21) Appl. No.: 10/017,143

(22) Filed: Oct. 29, 2001

(65) Prior Publication Data

US 2003/0032349 A1 Feb. 13, 2003

Related U.S. Application Data

(60) Provisional application No. 60/290,792, filed on May 14, 2001.

(51) Int. Cl.[7] .................................................. B32B 5/02
(52) U.S. Cl. ....................................... 442/123; 442/408
(58) Field of Search .................................. 442/123, 408

(56) References Cited

U.S. PATENT DOCUMENTS 5,863,663 A    1/1999   Mackey et al.
5,951,991 A    9/1999   Wagner et al.
5,952,043 A    9/1999   Mackey et al.
5,980,931 A   11/1999   Fowler et al.

FOREIGN PATENT DOCUMENTS

| EP | 0 613 675 | 4/1994 |
|---|---|---|
| EP | 1 149 674 | 4/2001 |
| WO | 95/17175 | 6/1995 |
| WO | 96/24329 | 8/1996 |
| WO | 97/40814 | 11/1997 |
| WO | 99/55303 | 11/1999 |
| WO | 01/08542 | 2/2001 |
| WO | 01/08655 | 2/2001 |
| WO | 01/08656 | 2/2001 |
| WO | 01/08657 | 2/2001 |
| WO | 01/08658 | 2/2001 |

*Primary Examiner*—Elizabeth M. Cole
(74) *Attorney, Agent, or Firm*—Milton L. Honig

(57) ABSTRACT

A disposable substantially damp cleansing article is disclosed having a cleansing composition impregnated onto a flexible substrate such as a non-woven cloth. The impregnated compositions include lathering surfactants and water, the compositions having a viscosity ranging from about 50 to about 300,000 centipoise. Amounts of water range from greater than 15% to no higher than about 40% by weight of the total article. Speed of lather formation and foam volume increases within the window of the stated viscosity and water range.

9 Claims, No Drawings

DAMP CLEANSING WIPE

This application claims benefit of provisional application 60/290,792 filed May 14, 2001.

BACKGROUND OF THE INVENTION

1. Field of the Invention

The invention concerns low-cost, easily manufacturable disposable single use, substantially damp, cleansing articles.

2. The Related Art

Personal cleansing and conditioning products have traditionally been marketed in a variety of forms such as bar soaps, creams, lotions, and gels. These formulations have attempted to satisfy a number of criteria to be acceptable to consumers. These criteria include cleansing effectiveness, skin feel, skin mildness and lather volume. Ideal personal cleansers should gently cleanse the skin or hair, cause little or no irritation, and not leave the skin or hair overly dry after frequent use.

A series of granted and pending patent applications have been published by Procter & Gamble describing disposable personal cleansing products purportedly addressing many of the aforementioned functionality concerns. These products are substantially dry articles having deposited onto a woven or non-woven cloth a cleansing composition of surfactant, structurant, skin conditioning agent and other performance ingredients. The term "substantially dry" is defined in most of these documents as maximum 10%, but in some instances as high as 15% water. Particularly preferred levels are 5% or less. A commercial embodiment sold in the U.S. is Olay® Daily Facial Cleansing Cloths having water levels of 3–4% by weight of the total cloth article. The technology is described in the following patents.

U.S. Pat. No. 5,951,991 (Wagner et al.) focuses on providing the substrate with a conditioning emulsion separately impregnated from the lathering surfactant onto the cloth substrate. U.S. Pat. No. 5,980,931 (Fowler et al.) emphasizes impregnation of oil soluble conditioning agents. WO 99/55303 (Albacarys et al.) describes skin care actives formulated with the cleansing composition.

Manufacturing processes for these products are reported in U.S. Pat. Nos. 5,952,043 and 5,863,663, both to Mackey et al. These patents teach use of a continuous lipid phase with a high melting waxy material deposited onto the wipe substrate. The material is intended to be sufficiently brittle so as to be easily disrupted by low shear contact (e.g. during wiping of the skin) to readily release an internal skin conditioning phase, yet the material is required to be sufficiently tough to avoid premature release of the internal phase during the rigors of processing. A problem with this technology is that through compromise the continuous external lipid phase/internal polar phase is neither sufficiently robust for processing and handling nor sufficiently releasable under wash conditions to allow efficient release of conditioning agent onto the skin.

More recent publications in this area include WO 01/08542 A1 (Cen et al.), WO 01/08655 A1 (Phipps et al.), WO 01/08656 A1 (Smith et al.), WO 01/08657 A1 (Lorenzi et al.) and WO 01/08658 A1 (Cawkwell et al.), all to Procter and Gamble. These documents extend the wipe technology to bonded double layer substrates of contrasting textural properties. A rougher of the two sides may act as a gripping surface while the other may be used for delivering cleansing aids. The articles are described as being substantially dry defined as a Moisture Retention ratio of less than 0.95 gms. The ratio reports weight for total non-bound liquids in the article but is not synonymous with water content. Water levels are not defined.

Our evaluations of dry wipes produced by the known technology has indicated slow latherability. We attribute the problem to the relatively thick coating deposited onto the wipe substrate. Another probable source of the problem is the relatively low water content. A need exists for a cleansing wipe of improved foamability and one which can be efficiently manufactured.

Accordingly, it is an object of the present invention to provide a disposable, cleansing product which upon contact with water rapidly lathers and generates a rich long lasting foam.

Another object of the present invention is to provide a disposable cleansing product having a cleansing composition coatable onto a flexible wiping cloth in a process that minimizes foam generation during manufacture.

Still another object of the present invention is to provide a disposable cleansing product which may include an impregnated composition allowing for improved manufacturability, better aesthetics and increased latherability.

These and other objects of the present invention will become more apparent in light of the following summary and disclosure.

SUMMARY OF THE INVENTION

A substantially damp cleansing product is provided which includes:
(i) a water insoluble substrate; and
(ii) a cleansing composition impregnated onto the substrate including:
   (a) at least one lathering surfactant present in an amount sufficient to foam;
   (b) water; and
   wherein the water is present at greater than 15% by weight of the product, but no higher than about 40%, and the composition having a viscosity as measured on a Haake CV 20 Rheometer with 30 mm profiled parallel plates at 23° C. ranging from about 50 to about 300,000 cp.

DETAILED DESCRIPTION OF THE INVENTION

Now it has been discovered that there is a critical range of viscosity for the impregnated cleansing composition. Below a minimum viscosity, the composition foams poorly when the dry wipe is wetted with water by a consumer. Although not wishing to be bound by a theory, we believe the low viscosity compositions are readily washed away by water down the sink and unavailable for lathering. By contrast, a too high viscosity composition cannot be quickly activated with water for lathering by a consumer. There is a delay period.

Accordingly, the compositions of the present invention will have a viscosity ranging from about 50 to about 300,000 cp (centipoise). Thickness is measured on a Haake CV 20 Rheometer with 30 mm profiled parallel plates at 23° C. A preferred viscosity range is from about 100 to about 250,000 cp, more preferably from about 150 to about 100,000, even more preferably from about 200 to about 50,000 cp, and optimally from about 400 to about 10,000 cp.

Another important discovery is the criticality of water levels. Substantially dry articles are poor at instantaneously generating a foam. Lathering surfactant cannot easily be activated at levels below 15% water. Some substantial amount of water must be present to allow the lathering surfactants to exit more rapidly from the substrate creating a foam. Minimum levels should be greater than 15%, preferably at least about 20%, more preferably at least about 25% by weight of the total cleansing product. These damp levels of water have the further advantage of giving pliability to the fabric substrate. A softer, more pleasant feel results.

Too much water should not be present. Large amounts of water impart a soggy poor aesthetic feel to the product. Even more significant, water encourages microbial growth. Much higher levels of preservatives are necessary with high water systems. Preservatives are not just a cost issue. Some consumers are hypoallergic to certain types of preservatives. Preserved systems must continuously be monitored to ensure that microbes have not mutated into strain resistant forms. Thus, maximum levels should be no higher than about 40% and preferably no higher than about 35% by weight of the cleansing product.

An essential element of compositions according to the present invention is that of a lathering surfactant. By a "lathering surfactant" is meant a surfactant, which when combined with water and mechanically agitated generates a foam or lather. Preferably, these lathering surfactants should be mild, which means that they must provide sufficient cleansing or detersive benefits but not overly dry the skin or hair, and yet meet the lathering criteria described above.

The products of the present invention typically include at least one lathering surfactant in an amount from about 0.5% to about 60%, preferably from about 0.75% to about 40%, and more preferably from about 1% to about 20%, based on the weight of the impregnated composition.

A wide variety of lathering surfactants are useful herein and include those selected from the group consisting of anionic, nonionic, cationic, amphoteric and lathering surfactant mixtures thereof.

Among the anionic lathering surfactants useful herein are the following non-limiting examples which include the classes of:

(1) Alkyl benzene sulfonates in which the alkyl group contains from 9 to 15 carbon atoms, preferably 11 to 14 carbon atoms in straight chain or branched chain configuration. Especially preferred is a linear alkyl benzene sulfonate containing about 12 carbon atoms in the alkyl chain.
(2) Alkyl sulfates obtained by sulfating an alcohol having 8 to 22 carbon atoms, preferably 12 to 16 carbon atoms. The alkyl sulfates have the formula $ROSO_3{}^-M^+$ where R is the $C_{8-22}$ alkyl group and M is a mono- and/or divalent cation.
(3) Paraffin sulfonates having 8 to 22 carbon atoms, preferably 12 to 16 carbon atoms, in the alkyl moiety. These surfactants are commercially available as Hostapur SAS from Hoechst Celanese.
(4) Olefin sulfonates having 8 to 22 carbon atoms, preferably 12 to 16 carbon atoms. Most preferred is sodium $C_{14}$–$C_{16}$ olefin sulfonate, available as Bioterge AS 40®
(5) Alkyl ether sulfates derived from an alcohol having 8 to 22 carbon atoms, preferably 12 to 16 carbon atoms, ethoxylated with less than 30, preferably less than 12, moles of ethylene oxide. Most preferred is sodium lauryl ether sulfate formed from 2 moles average ethoxylation, commercially available as Standopol ES-2®.
(6) Alkyl glyceryl ether sulfonates having 8 to 22 carbon atoms, preferably 12 to 16 carbon atoms, in the alkyl moiety.
(7) Fatty acid ester sulfonates of the formula: $R^1CH(SO_3{}^-M+)CO_2R^2$ where $R^1$ is straight or branched alkyl from about $C_8$- to $C_{18}$, preferably $C_{12}$ to $C_{16}$, and $R^2$ is straight or branched alkyl from about $C_1$ to $C_6$, preferably primarily $C_1$, and M+ represents a mono- or divalent cation.
(8) Secondary alcohol sulfates having 6 to 18, preferably 8 to 16 carbon atoms.
(9) Fatty acyl isethionates having from 10 to 22 carbon atoms, with sodium cocoyl isethionate being preferred.
(10) Dialkyl sulfosuccinates wherein the alkyl groups range from 3 to 20 carbon atoms each.
(11) Alkanoyl sarcosinates corresponding to the formula $RCON(CH_3)CH_2CH_2CO_2M$ wherein R is alkyl or alkenyl of about 10 to about 20 carbon atoms and M is a water-soluble cation such as ammonium, sodium, potassium and trialkanolammonium. Most preferred is sodium lauroyl sarcosinate.
(12) Alkyl lactylates wherein the alkyl groups range from 8 to 12 carbon atoms, with sodium lauroyl lactylate sold as Pationic 138C® available from the Patterson Chemical Company as the most preferred.
(13) Taurates having from 8 to 16 carbon atoms, with cocoyl methyl taurate being preferred.

Nonionic lathering surfactants suitable for the present invention include $C_{10}$–$C_{20}$ fatty alcohol or acid hydrophobes condensed with from 2 to 100 moles of ethylene oxide or propylene oxide per mole of hydrophobe; $C_2$–$C_{10}$ alkyl phenols condensed with from 2 to 20 moles of alkylene oxides; mono- and di- fatty acid esters of ethylene glycol such as ethylene glycol distearate; fatty acid monoglycerides; sorbitan mono- and di-$C_8$–$C_{20}$ fatty acids; and polyoxyethylene sorbitan available as Polysorbate 80 and Tween 80® as well as combinations of any of the above surfactants.

Other useful nonionic surfactants include alkyl polyglucosides, saccharide fatty amides (e.g. methyl gluconamides) as well as long chain tertiary amine oxides. Examples of the latter category are: dimethylododecylamine oxide, oleyldi(2-hydroxyethyl)amine oxide, dimethyloctylamine oxide, dimethyldecylamine oxide, dimethyltetradecylamine oxide, di(2-ydroxyethyl)tetradecylamine oxide, 3-didodecyloxy-2-hydroxypropyldi(3-hydroxypropyl) amine oxide, and dimethylhexadecylamine oxide.

Amphoteric lathering surfactants useful for the present invention include aliphatic secondary and tertiary amines, preferably wherein the nitrogen is in a cationic state, in which the aliphatic radicals can be straight or branched chain and wherein one of the radicals contains an ionizable water solubilizing group such as carboxy, sulphonate, sulphate, phosphate or phosphonate. Illustrative substances are cocamidopropyl betaine, cocamphoacetate, cocamphodiacetate, cocamphopropionate, cocamphodipropionate, cocamidopropyl hydroxysultaine, cetyl dimethyl betaine, cocamidopropyl PG-dimonium chloride phosphate, coco dimethyl carboxymethyl betaine, cetyl dimethyl betaine and combinations thereof.

For purposes of the present invention, the total of all lathering surfactants to water may be in a weight ratio ranging from about 1:10 to about 5:1, preferably from about 1:4 to about 4:1, more preferably from about 1:3 to about 3:1, and optimally from about 1:2 to about 2:1.

A necessary element of the present invention is that of a water insoluble substrate. By "water insoluble" is meant the substrate does not dissolve or readily break apart upon immersion in water. A wide variety of materials can be used as the substrate. The following non-limiting characteristics are desirable: (i) sufficient wet strength for use, (ii) sufficient abrasivity, (iii) sufficient loft and porosity, (iv) sufficient thickness, and (v) appropriate size.

Non-limiting examples of suitable insoluble substrates which meet the above criteria include non-woven substrates, woven substrates, hydro-entangled substrates, air entangled substrates and the like. Preferred embodiments employ non-woven substrates since they are economical and readily available in a variety of materials. By non-woven is meant that the layer is comprised of fibers which are not woven into a fabric but rather are formed into a sheet, particularly a tissue. The fibers can either be random (i.e., randomly aligned) or they can be carded (i.e. combed to be oriented in primarily one direction). Furthermore, the non-woven substrate can be composed of a combination of layers of random and carded fibers.

Non-woven substrates may be comprised of a variety of materials both natural and synthetic. By natural is meant that the materials are derived from plants, animals, insects or byproducts. By synthetic is meant that the materials are obtained primarily from various man-made materials or from material that is usually a fibrous web comprising any of the common synthetic or natural textile-length fibers, or mixtures thereof.

Non-limiting examples of natural materials useful in the present invention are silk fibers, keratin fibers and cellulosic fibers. Non-limiting examples of keratin fibers include those selected from the group consisting of wool fibers, camel hair fibers, and the like. Non-limiting examples of cellulosic fibers include those selected from the group consisting of wood pulp fibers, cotton fibers, hemp fibers, jute fibers, flax fibers, and mixtures thereof.

Non-limiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers and mixtures thereof. Examples of some of these synthetic materials include acrylics such as Acrilan®, Creslan®, and the acrylonitrile-based fiber, Orion®; cellulose ester fibers such as cellulose acetate, Arnel®, and Acele®; polyamides such as Nylons (e.g., Nylon 6, Nylon 66, and Nylon 610); polyesters such as Fortrel®, Kodel®, and Dacron®; polyolefins such as polypropylene, polyethylene; polyvinyl acetate fibers and mixtures thereof.

Non-woven substrates made from natural materials consist of webs or sheets most commonly formed on a fine wire screen from a liquid suspension of the fibers.

Substrates made from natural materials useful in the present invention can be obtained from a wide variety of commercial sources. Non-limiting examples of suitable commercially available paper layers useful herein include Airtex®, an embossed airlaid cellulosic layer having a base weight of about 71 gsy, available from James River Corporation, Green Bay, Wis.; and Walkisoft®, an embossed airlaid cellulosic having a base weight of about 75 gsy, available from Walkisoft U.S.A., Mount Holly, N.C.

Non-woven substrates made from synthetic material useful in the present invention can also be obtained form a wide variety of commercial sources. Non-limiting examples of suitable non-woven layer materials useful herein include HFE-40-047, an apertured hydroentangled material containing about 50% rayon and 50% polyester, and having a basis weight of about 43 grams per square yard (gsy), available from Vertec, Inc., Walpole, Mass.; HEF 140-102, an apertured hydro-entangled material containing about 50% rayon and 50% polyester, and having a basis weight of about 56 gsy, available from Veratec, Inc., Walpole, Mass.; Novenet® 149-191, a thermo-bonded grid patterned material containing about 69% rayon, about 25% polypropylene, and about 6% cotton, and having a basis weight of about 100 gsy, available from Veratec, Inc., Walpole, Mass.; HEF Nubtex® 149-801, a nubbed, apertured hydro-entangled material, containing about 100% polyester, and having a basis weight of about 70 gsy, available from Veratec, Inc. Walpole, Mass.; Keybak® 951V, a dry formed apertured material, containing about 75% rayon, about 25% acrylic fibers, and having a basis weight of about 43 gsy, available from Chicopee Corporation, New Brunswick, N.J.; Keybak® 1368, an apertured material, containing about 75% rayon, about 5% polyester, and having a basis weight of about 39 gsy, available from Chicopee Corporation, New Brunswick, N.J.; Duralace® 1236, an apertured, hydro-entangled material, containing about 100% rayon, and having a basis weight from about 40 gsy to about 115 gsy, available from Chicopee Corporation, New Brunswick, N.J.; Duralace® 5904, an apertured, hydro-entangled material, containing about 100% polyester, and having a basis weight from about 40 gsy to about 115 gsy, available from Chicopee Corporation, New Brunswick, N.J.; Sontaro® 8868, a hydro-entangled material, containing about 50% cellulose and about 50% polyester, and having a basis weight of about 60 gsy, available from Dupont Chemical Corp.

Most preferred as a substrate for purposes of this invention are non-woven substrates, especially blends of rayon/polyester and ratios of 10:90 to 90:10, preferably ratios of 20:80 to 80:20, optimally 40:60 to 60:40 by weight. A most useful substrate is a 70:30 rayon/polyester non-woven wipe article.

Anywhere from 1 to 100, preferably from 5 to 50 single wipes may be stored within a dispensing pouch or container, preferably a moisture impermeable pouch or container. During storage and between dispensing, the pouch or container is preferably resealable. Single wipe containing pouches may also be employed.

The water insoluble substrates of the present invention can comprise two or more layers, each having a different texture and abrasiveness. The differing textures can result from the use of different combinations of materials or from the use of a substrate having a more abrasive side for exfoliation and a softer, absorbent side for gentle cleansing. In addition, separate layers of the substrate can be manufactured to have different colors, thereby helping the user to further distinguish the surfaces. Although the present invention may be suitable for substrates with two or more layers having different texture and abrasiveness, the best effectiveness of the damp system can be found with single or multiple layered substrates of identical construction.

The amount of impregnating composition relative to the substrate may range from about 20:1 to 1:20, preferably from 10:1 to about 1:10 and optimally from about 2:1 to about 1:2 by weight.

Impregnating compositions of the present invention may also include silicones of a volatile and non-volatile variety. Typical volatile silicones are the cyclomethicones commercially available as Dow Corning 244, 245, 344 and 345. Linear volatile dimethicones are also suitable. Non-volatile silicones include polydimethyl siloxanes of a viscosity greater than 2 centistoke and silicone copolyols also known as dimethicone copolyol for which Dow Corning 193 is a commercial source. Amounts of the silicones may range from about 0.01 to about 20, preferably from about 0.5 to about 3% by weight of the impregnated composition.

Cationic conditioning agents in monomeric and polymeric type are also useful for purposes of this invention.

Examples of the polymeric type include: cationic cellulose derivatives, cationic starches, copolymers of a diallyl quaternary ammonium salt and an acrylamide, quaternized vinylpyrrolidone vinylimidazole polymers polyglycol amine condensates, quaternized collagen polypeptide, polyethylene imine, cationized silicon polymer (e.g. Amodimethicone), cationic silicon polymers provided in a mixture with other components under the trademark Dow Corning 929 (cationized emulsion), copolymers of adipic acid and dimethylaminohydroxypropyl diethylenetriamine, cationic chitin derivatives, cationized guar gum (e.g. Jaguar C-B-S, Jaguar C-17, Jaguar C-16 etc. manufactured by the Celanese Company), quaternary ammonium salt polymers (e.g. Mirapol A-15, Mirapol AD-1, Mirapol AZ-1, etc., manufactured by the Miranol Division of the Rhone Poulenc Company). Most preferred is polyquaternium-11 available as Luviquat® PQ 11 sold by the BASF Corporation.

Examples of monomeric cationic conditioning agents are salts of the general structure:

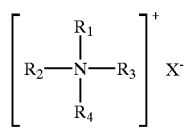

wherein $R^1$ is selected from an alkyl group having from 12 to 22 carbon atoms, or aromatic, aryl or alkaryl groups having from 12 to 22 carbon atoms; $R^2$, $R^3$, and $R^4$ are independently selected from hydrogen, an alkyl group having from 1 to 22 carbon atoms, or aromatic, aryl or alkaryl groups having from 12 to 22 carbon atoms; and $X^-$ is an anion selected from chloride, bromide, iodide, acetate, phosphate, nitrate, sulfate, methyl sulfate, ethyl sulfate, tosylate, lactylate, citrate, glycolate, and mixtures thereof. Additionally, the alkyl groups can also contain ether linkages, or hydroxy or amino group substituents (e.g. the alkyl groups can contain polyethylene glycol and polypropylene glycol moieties). Preferably the anion is phosphate, especially preferred is hydroxy ethyl cetyl dimonium phosphate available as Luviquat® Mono CP from the BASF Corporation.

Amino silicones quats may similarly be employed. Most preferred is Silquat AD designated by the CTFA as Silicone Quaternium 8, available from Siltech Inc.

Amounts of each cationic agent may range from about 0.05 to about 5%, preferably from about 0.1 to about 3%, optimally from about 0.3 to about 2.5% by weight of the impregnated composition.

Water-binding agents are preferably included in compositions of the present invention. Water soluble binding agents such as polyhydric alcohols are particularly preferred. Typical polyhydric alcohols include glycerol (also known as glycerin), polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the water-binding agent is preferably glycerin. Also particularly preferred are polyethylene glycol (average molecular weight ranging from about 200 to about 2,000,000, with PEG-9M and PEG-14M being preferred) and hexylene glycol. In certain types of compositions the latter agent may be inappropriate and therefore polyols other than hexylene glycol should be utilized. The amount of water-binding agent may range anywhere from about 0.5 to about 50%, preferably between about 1 and about 30% by weight of the composition.

The disposable, single use personal care cleansing products of the present invention are manufactured by separately or simultaneously adding onto or impregnating into a water insoluble substrate the cleansing composition including lathering surfactants and conditioners, wherein the resulting product is substantially dry. By "separately" is meant that the surfactants and the conditioners can be added sequentially, in any order without first being combined together. By "simultaneously" is meant that the surfactants and conditioners can be added at the same time, with or without first being combined together.

The surfactant, conditioners, water-binding agents and any other optional ingredients can be added onto or impregnated into the water insoluble substrate by any means known to those skilled in the art. For example, addition can be through spraying, laser printing, splashing, dipping, soaking, or coating.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

The following examples will more fully illustrate the embodiments of this invention. All parts, percentages and proportions referred to herein and in the appended claims are by weight unless otherwise illustrated.

EXAMPLE 1

A formula typical of the present invention for impregnation onto a rayon/polyester substrate was formulated with the following components.

TABLE I

Example 1 Formula

| INGREDIENT | WEIGHT % |
|---|---|
| Deionized Water | 25.45 |
| Glycerin | 25.00 |
| Cocamidopropyl Betaine (Tegobetaine F ®, 30% Active) | 18.23 |
| Sodium Lauroyl Sarcosinate (Hamposyl L-30 ®, 30% Active) | 18.23 |
| Decyl Polyglucoside (Plantareen 2000 N ®, 50% Active) | 11.15 |
| Silicone Quaternium-8 (Hanisquat AD ®, 40% Active) | 0.50 |
| Polyquaternium 10 (Celquat SC-230M ®) | 0.40 |
| Fragrance | 0.40 |
| Sodium Lauroyl Lactylate (Pationic 138C ®) | 0.20 |
| Polyquaternium 4 (Celquat L-200 ®) | 0.15 |
| Methyl Paraben | 0.15 |
| Preservatives | 0.10 |
| Soya Sterol (Generol 122 ®) | 0.01 |
| Cholesterol | 0.01 |
| Vitamin E Acetate | 0.01 |
| Vitamin A Palmitate | 0.01 |

The formula of the Table was coated onto a substrate at 2.0 grams coating per 2.0 grams rayon/polyester sheet (752 mm by 190 mm area).

Lather quality/stability comparisons were conducted on this Example. A modified Ross-Miles foam tester was employed. The towelettes lather parameters were measured on 3 cloths in 200 ml of water. Results are reported in the Table below.

TABLE II

Lather Quality/Stability Comparison

| Sample | Lather Quality/Stability* | Lather Height (ml) |
|---|---|---|
| Olay ® Daily Facial Cleansing Cloths** | 3 | 400 |
| Dove ® Daily Facial Cleansing Cloths | 3 | 550 |
| Example 1 (coated on towelette) | 4.5 | 500 |

*Scale of 1 to 5, in order of increasing lather quality/stability.
**Representative of towelettes described by P&G in U.S. Pat. No. 5,951,991, U.S. Pat. No. 5,980,931, U.S. Pat. No. 5,952,043, U.S. Pat. No. 5,863,663 and WO 99/55303

A consumer study was also conducted on two of the towelette types described above. The study was based on response by 118 panelists. Results are reported in Table III below.

TABLE III

Consumer Test

| | % Preferred | |
|---|---|---|
| Property | Example 1 Formula (Coated on Towelette) | Olay ® Daily Facial Cleansing Cloths |
| Having a creamy lather | 72 | 28 |
| Lathers quickly | 68 | 32 |
| Leaves skin feeling soft | 61 | 39 |
| Leaves skin feeling moisturized | 59 | 41 |

Based upon the findings reported in Table III, there was a significant preference for the Example 1 formula towelette which incorporated 25% water. The Olay® towelette with only 3–4% water did not provide a sufficiently creamy lather, lathered slower, left skin feeling less soft and less moisturized than the towelette of the present invention.

EXAMPLE 2

A series of compositions are presented under Table IV reflective of the present invention. These compositions are impregnated onto a non-woven polyester substrate at a 1:1 weight ratio.

TABLE IV

| INGREDIENT | A | B | C | D | E | F | G |
|---|---|---|---|---|---|---|---|
| Hexylene Glycol | 15.00 | 13.45 | 11.00 | — | 19.45 | 29.00 | — |
| Butylene Glycol | — | 2.00 | 4.00 | 15.00 | — | — | 19.00 |
| Water | 25.00 | 25.00 | 25.00 | 25.00 | 25.00 | 30.00 | 30.00 |
| Polyquaternium (Polymer JR 400 ®) | 1.00 | — | — | — | — | — | — |
| PEG 9M (PEO-2) | — | — | — | 1.00 | — | — | 1.00 |
| Polyquaternium 4 (Celquat L-200 ®) | — | 0.15 | — | — | 0.15 | — | — |
| Polyquaternium 4 (Celquat L-230M ®) | — | 0.40 | — | — | 0.40 | — | — |
| Hydroxypropyl Cellulose (Klucel GF ®) | — | — | 1.00 | — | — | 1.00 | — |
| Polyquaternium 7 (Merquat 2200 ®) | 1.33 | 1.33 | 1.33 | 1.33 | — | — | — |
| Cocamidopropyl Betaine (Tegobetaine F ®; 30% Active) | 17.60 | 17.60 | 17.60 | 17.60 | 20.00 | 20.00 | 20.00 |
| Decyl Polyglucoside (Plantaren 2000N ®; 50% Active in Water) | 11.00 | 11.00 | 11.00 | 11.00 | 15.00 | — | — |
| Sodium Lauroyl Sarcosinate (Hamposyl L-30 ®; 30% Active) | 17.60 | 17.60 | 17.60 | 17.60 | 20.00 | 20.00 | 30.00 |
| Sodium Lauroyl Lactylate (Pationic 138C ®) | 1.74 | 1.74 | 1.74 | 1.74 | — | — | — |
| Capric/Caprylic Triglycerides (Miglyol 812 ®) | 2.50 | 2.50 | 2.50 | 2.50 | — | — | — |
| Silicon Quaternium-8 (Silquat AD ®; 40% Active in Water) | 6.00 | 6.00 | 6.00 | 6.00 | — | — | — |
| Fragrance | 1.03 | 1.03 | 1.03 | 1.03 | — | — | — |
| Glydant Plus ® Liquid (DMDM Hydantoin and Iodopropynyl Butylcarbamate in Butylene Glycol) | 0.20 | 0.20 | 0.20 | 0.20 | — | — | — |

| INGREDIENT | H | I | J | K | L | M | N |
|---|---|---|---|---|---|---|---|
| Hexylene Glycol | — | 3.50 | 14.00 | — | — | — | — |
| Butylene Glycol | — | — | — | — | — | 24.30 | — |
| Glycerin | 19.00 | 19.45 | — | 18.3 | 29.45 | — | 32.30 |
| Water | 20.00 | 20.00 | 14.08 | 20.00 | 18.00 | 24.45 | 15.00 |
| Polyquaternium (Polymer JR 400 ®) | 1.00 | — | — | — | — | — | — |
| PEG 9M (PEO-2) | — | — | — | — | — | — | — |
| Polyquaternium 4 (Celquat L-200 ®) | — | 0.15 | — | — | 0.15 | 0.15 | — |
| Polyquaternium 4 (Celquat L-230M ®) | — | 0.40 | — | — | 0.40 | 0.40 | — |
| Hydroxypropyl Cellulose (Klucel GF ®) | — | — | 1.00 | 1.00 | — | — | 1.00 |
| Sodium Laureth Sulfate, 2 mol, 70% in water (Steol ® CS 270) | — | 20.00 | — | — | 28.00 | 25.00 | 25.00 |
| Polyquaternium 7 (Merquat 2200 ®) | — | 1.00 | — | 1.00 | — | — | 1.00 |
| Cocamidopropyl Betaine (Tegobetaine F ®; 30% Active) | 16.12 | 30.00 | 14.07 | 27.00 | 18.00 | 15.00 | 20.0 |

TABLE IV-continued

| Ingredient | | | | | | | |
|---|---|---|---|---|---|---|---|
| Decyl Polyglucoside (Plantaren 2000N ®; 50% Active in Water) | 16.00 | — | 28.15 | — | — | — | — |
| Sodium Lauroyl Sarcosinate (Hamposyl L-30 ®; 30% Active) | 14.13 | — | — | 27.00 | — | — | — |
| Sodium Lauroyl Lactylate (Pationic 138C ®) | 2.00 | — | — | — | — | — | — |
| Capric/Caprylic Triglycerides (Miglyol 812 ®) | 5.00 | 5.00 | 5.00 | 5.00 | 3.00 | — | — |
| Dimethicone (D/C 200 fluid) | — | — | — | — | — | 10.00 | — |
| Sunflowerseed oil (Cropure Sunflower) | — | — | 20.00 | — | — | — | 5.00 |
| Petrolatum | — | — | 3.00 | — | 2.50 | — | — |
| Silicone Quaternium-8 (Silquat AD ®; 40% Active in Water) | 6.00 | — | — | — | — | — | — |
| Fragrance | 0.50 | 0.50 | 0.50 | 0.50 | 0.50 | 0.50 | 0.50 |
| Glydant Plus ® Liquid (DMDM Hydantoin and Iodopropynyl Butylcarbamate in Butylene Glycol) | 0.25 | — | 0.20 | 0.20 | — | 0.20 | 0.20 |

| | SAMPLE (Weight %) | | | | |
|---|---|---|---|---|---|
| INGREDIENT | O | P | Q | R | S |
| Hexylene Glycol | 14.50 | 18.75 | — | — | — |
| Butylene Glycol | — | — | — | — | — |
| Glycerin | — | — | 18.30 | — | — |
| Water | 20.00 | 35.00 | 35.00 | 18.30 | 18.30 |
| PEG 9M (PEO-2) | — | — | — | — | 1.00 |
| Polyquaternium 4 (Celquat L-200 ®) | — | 0.15 | — | — | — |
| Polyquaternium 4 (Celquat L-230M ®) | — | 0.40 | — | — | — |
| Hydroxypropyl Cellulose (Klucel GF ®) | 1.00 | — | 1.00 | — | — |
| Sodium Laureth Sulfate, 2 mol, 70% in water (Steol CS ® 270) | — | — | — | 35.00 | 35.00 |
| Polyquaternium 10 (Polymer JR ® 400) | 2.00 | 1.00 | — | 1.00 | 1.00 |
| Polyquaternium 7 (Merquat 2200 ®) | — | — | 1.00 | 1.00 | — |
| Cocamidopropyl Betaine (Tegobetaine F ®; 30% Active) | 18.00 | — | 18.00 | 18.00 | — |
| Decyl Polyglucoside (Plantaren 2000N ®; 50% Active in Water) | 16.00 | 40.00 | 22.00 | 22.00 | 40.00 |
| Sodium Lauroyl Sarcosinate (Hamposyl L-30 ®; 30% Active) | 18.00 | — | — | — | — |
| Sodium Lauroyl Lactylate (Pationic 138C ®) | 1.00 | — | — | — | — |
| Capric/Caprylic Triglycerides (Miglyol 812 ®) | 3.00 | — | — | — | — |
| Dimethicone (D/C 200 fluid) | — | — | — | — | — |
| Sunflowerseed oil (Cropure Sunflower) | — | 3.00 | 3.00 | 3.00 | 3.00 |
| Petrolatum | — | 1.00 | 1.00 | 1.00 | 1.00 |
| Silicone Quaternium-8 (Silquat AD ®; 40% Active in Water) | 6.00 | — | — | — | — |
| Fragrance | 0.30 | 0.50 | 0.50 | 0.50 | 0.50 |
| Glydant Plus ® Liquid (DMDM Hydantoin and Iodopropynyl Butylcarbamate in Butylene Glycol) | 0.20 | 0.20 | 0.20 | 0.20 | 0.20 |

EXAMPLE 3

This Example reports on impregnation composition viscosities and their effect upon lather properties. Three formulations were prepared. These are reported in the Table below.

TABLE V

| | SAMPLE (WEIGHT %) | | |
|---|---|---|---|
| INGREDIENT* | A | B | C |
| Water | 48.30 | 48.30 | 48.30 |
| Sodium laureth sulfate, 2 moles ethoxylation, 30% in water (Steol CS-230 ® Low Salt, Stepan) | 35.00 | 35.00 | 35.00 |
| Cocamidopropyl betaine, 30% in water (Tegobetaine F ®, Goldschmidt) | 14.70 | 14.70 | 14.70 |
| Sodium Chloride | 2.00 | 0.00 | 1.00 |
| Hexylene Glycol | 0.00 | 2.00 | 1.00 |
| Viscosity (cp)** | 290,100 | 21.4 | 12,770 |

*Loading = 1.3 grams per 752 mm by 190 mm towelette
Fabric = 65 grams/m² formed of rayon/polyester blend
**Haake CV 20 Rheometer with 30 mm profiled parallel plates at RT

TABLE VI

| | Lather Results | | | | | |
|---|---|---|---|---|---|---|
| | Sample A | | Sample B | | Sample C | |
| | Quick Lather | Lather Amount | Quick Lather | Lather Amount | Quick Lather | Lather Amount |
| Panelist 1 | 2 | 5 | 5 | 1 | 5 | 4 |
| Panelist 2 | 2 | 4 | 5 | 1 | 5 | 5 |
| Panelist 3 | 2 | 4 | 4 | 3 | 4 | 4 |
| Panelist 4 | 4 | 5 | 5 | 4 | 5 | 5 |
| Panelist 5 | 2 | 3 | 4 | 3 | 4 | 4 |
| Panelist 6 | 1 | 5 | 5 | 2 | 5 | 5 |
| Panelist 7 | 2 | 4 | 4 | 2 | 4 | 4 |
| Average | 2.14 | 4.29 | 4.57 | 2.29 | 4.57 | 4.43 |

The Panel Test results recorded in Table VI involved the Samples A–C impregnated towelettes being wetted under running water for 3 seconds. Thereafter the towelette was manipulated to generate lather. The Scale was: 5=fast (high) and 1=slow (little).

Sample A is a relatively high viscosity impregnated composition. While a satisfactory amount of lather was obtained, the generation was slow. Sample B with a relatively thin viscosity impregnated composition was quick to lather but total amount was relatively low. Sample C was a towelette loaded with a mid-range viscosity composition. It created a good amount of lather and was generated in a short period of time.

The foregoing description and examples illustrate selected embodiments of the present invention. In light thereof variations and modifications will be suggested to one skilled in the art, all of which are within the spirit and purview of this invention.

What is claimed is:

1. A substantially damp cleansing product comprising:
   (i) a water insoluble substrate; and
   (ii) a cleansing composition impregnated onto the substrate comprising:
      (a) from about 15% to about 60% by weight of impregnating composition of lathering surfactants;
      (b) water; and
   wherein the water is present at greater than 15% by weight of the product, but no higher than about 40%, and the composition having a viscosity as measured on a Haake CV 20 Rheometer with 30 mm profiled parallel plates at 23° C. ranging from about 50 to about 300,000 cp.

2. The product according to claim 1 wherein the viscosity ranges from about 100 to about 250,000 cp.

3. The product according to claim 1 wherein the viscosity ranges from about 150 to about 100,000 cp.

4. The product according to claim 1 wherein the viscosity ranges from about 400 to about 10,000 cp.

5. The product according to claim 1 wherein the weight ratio of all lathering surfactants to water ranges from about 1:10 to about 5:1.

6. The product according to claim 1 wherein the water insoluble substrate is a sheet selected from a group consisting of non-woven, woven, hydro-entangled and air entangled substrates.

7. A substantially damp cleansing product comprising:
   (i) a water insoluble substrate; and
   (ii) a cleansing composition impregnated onto the substrate comprising:
      (a) at least one anionic lathering surfactant present in an amount sufficient to foam;
      (b) water; and
   wherein the water is present in an amount of at least about 20% by weight of the product, but no higher than about 40%, and the composition having a viscosity as measured on a Haake CV 20 Rheometer with 30 mm profiled parallel plates at 23° C. ranging from about 10,0000 to about 300,000 cp.

8. A substantially damp cleansing product comprising:
   (i) a water insoluble substrate; and
   (ii) a cleansing composition impregnated onto the substrate comprising:
      (a) from about 15 % to about 60% by weight of the impregnated composition of lathering surfactant;
      (b) water; and
   wherein the water is in an amount of at least about 20% by weight of the product but no higher than about 40%, and the composition having a viscosity as measured on a Haake CV 20 Rheometer with 30 mm profiled parallel plates at 23° C. ranging from about 10,0000 to about 300,000 cp.

9. A substantially damp cleansing product comprising:
   (i) a water insoluble substrate; and
   (ii) a cleansing composition impregnated onto the substrate comprising:
      (a) from about 15 % to about 60% by weight of the composition of at least one lathering surfactant;
      (b) water; and
   wherein the water is present in an amount of at least about 25% by weight of the product, but no higher than about 40%, and the composition having a viscosity as measured on a Haake CV 20 Rheometer with 30 mm profiled parallel plates at 23° C. ranging from about 150 to about 100,000 cp.

* * * * *

UNITED STATES PATENT AND TRADEMARK OFFICE
CERTIFICATE OF CORRECTION

PATENT NO.         : 6,730,621 B2
APPLICATION NO. : 10/017143
DATED                 : May 4, 2004
INVENTOR(S)       : Gott et al.

It is certified that error appears in the above-identified patent and that said Letters Patent is hereby corrected as shown below:

Column 14, line 10, wherein "10,0000 to about 300,000 cp." should have read -- 10,000 to about 300,000 cp. --; and Claim 8, Column 14, line 23, wherein "10,0000 to about 300,000 cp." Should have read -- 10,000 to about 300,000 cp. --

Signed and Sealed this

Twenty-eighth Day of October, 2008

JON W. DUDAS
*Director of the United States Patent and Trademark Office*